United States Patent
Rao et al.

(10) Patent No.: US 9,428,444 B2
(45) Date of Patent: Aug. 30, 2016

(54) PROCESS FOR THE PREPARATION OF LEVOTHYROXINE SODIUM

(71) Applicant: AZICO BIOPHORE INDIA PRIVATE LIMITED, Hyderabad (IN)

(72) Inventors: Ch. A. P. Rameswara Rao, Hyderabad (IN); Sreenath Dasari, Hyderabad (IN)

(73) Assignee: AZICO BIOPHORE INDIA PRIVATE LIMITED, Hyderabad, Telangana (IN)

( * ) Notice: Subject to any disclaimer, the term of this patent is extended or adjusted under 35 U.S.C. 154(b) by 0 days.

(21) Appl. No.: 14/907,048

(22) PCT Filed: Jan. 30, 2014

(86) PCT No.: PCT/IB2014/058662
§ 371 (c)(1),
(2) Date: Jan. 22, 2016

(87) PCT Pub. No.: WO2015/011573
PCT Pub. Date: Jan. 29, 2015

(65) Prior Publication Data
US 2016/0168076 A1     Jun. 16, 2016

(30) Foreign Application Priority Data
Jul. 24, 2013  (IN) .......................... 3309/CHE/2013

(51) Int. Cl.
*C07C 59/00*     (2006.01)
*C07C 229/08*    (2006.01)

(52) U.S. Cl.
CPC .................................. *C07C 229/08* (2013.01)

(58) Field of Classification Search
CPC .................................................. C07C 229/08
USPC ............................................................ 562/465
See application file for complete search history.

(56) References Cited

U.S. PATENT DOCUMENTS

| | | | | |
|---|---|---|---|---|
| 2,886,592 A | * | 5/1959 | Hillmann | C07C 227/16 560/40 |
| 2,889,363 A | * | 6/1959 | Ginger | C07C 227/16 560/40 |
| 3,149,153 A | | 9/1964 | Blank et al. | |
| 3,374,269 A | | 3/1968 | Langer et al. | |
| 5,917,087 A | * | 6/1999 | Coe | C07C 227/16 560/39 |

FOREIGN PATENT DOCUMENTS

| | | | |
|---|---|---|---|
| WO | 2009/136249 A1 | 11/2009 | |
| WO | WO 2009136249 A1 | * 11/2009 | ............ C07C 227/16 |

OTHER PUBLICATIONS

Reddy et al 'Chemistry of thyroxine: an historical perspective and recent progress on its synthesis,' Tetrahedron, vol. 66, No. 11,Mar. 13, 2010 p. 195571962.*
Reddy et al., "Chemistry of thyroxine: an historical perspective and recent progress on its synthesis," Tetrahedron, vol. 36, No. 11, Mar. 13, 2010 pp. 1955-1962 (Cited in PCT/IB2014/058662 by USPTO in ISA).

* cited by examiner

*Primary Examiner* — Deborah D Carr
(74) *Attorney, Agent, or Firm* — Volpe and Koenig, P.C.

(57) ABSTRACT

The present invention provides a novel process for the preparation of highly pure Levothyroxine Sodium, i.e., (S)-2-amino-3-[4-(4-hydroxy-3, 5-diiodophenoxy)-3,5-diiodophenyl] propanoic acid sodium salt via two process intermediates viz 3,5-Diiodo L-Tyrosine copper complex and novel Bis (p-anisyl) iodonium Iodide. The invention also provides levothyroxine pentahydrate free from genotoxic impurities and liothyronine levels below 0.04% wt/wt.

2 Claims, No Drawings

PROCESS FOR THE PREPARATION OF LEVOTHYROXINE SODIUM

CROSS REFERENCE TO RELATED APPLICATIONS

This application is a 35 USC §371 national stage application of PCT/IB2014/058662, which was filed Jan. 30, 2014 and claimed priority to Indian Patent Application No. 3309/CHE/2013, filed Jul. 24, 2013, both of which are incorporated herein by reference as if fully set forth.

FIELD OF THE INVENTION

The present invention relates to a novel process for the preparation of pure Levothyroxine Sodium, i.e., (S)-2-amino-3-[4-(4-hydroxy-3,5-diiodophenoxy)-3,5-diiodophenyl]propanoic acid sodium salt via two process intermediates viz 3,5-Diiodo L-Tyrosine copper complex and novel Bis (p-anisyl) iodonium Iodide.

BACKGROUND OF THE INVENTION

Levothyroxine Sodium is a synthetic form of thyroid hormone Thyroxine, which is secreted from follicular cells of thyroid gland. Levothyroxine is ideally used for the treatment of thyroid hormone deficiencies such as hypothyroidism. Due to its ability to lower thyroid-stimulating hormone, Levothyroxine is also used in the treatment of goiter and also to prevent the recurrence of thyroid cancer.

Levothyroxine Sodium has the following chemical structure.

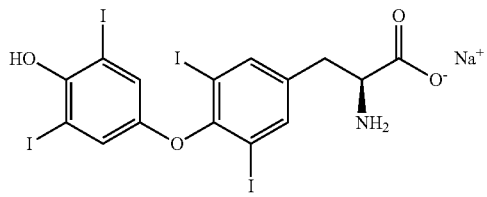 [SMILES: N[C@@H](Cc1cc(I)c(Oc2cc(I)c(O)c(I)c2)c(I)c1)C(=O)[O-] ; [Na+]]

For the preparation of Levothyroxine Sodium several methods have been known. U.S. Pat. No. 2,889,363 demonstrates the use of animal natural sources as starting material for the preparation of thyroxine while U.S. Pat. No. 2,889,364 discloses an enzymatic or bio-mimetic method of synthesis for levothyroxine.

The invention disclosed in U.S. Pat. No. 2,889,363 provides a process for the production of esters of N-acylthyroxine with a substantial reduction in the time period and involves digestive coupling reactions in which alkyl esters of N-acyldiidotyrosine yield alkyl esters of N-acylthyroxine in a greatly reduced time in the presence of optimal catalyst concentration, pH range and alcohol concentration. This prior art further involves a process for production of thyroxine by incubating alkyl esters of N-acyldiidotyrosine derived from lower alkanols and lower alkanoic acids in aqueous solution of ethanol (70%) of pH of 9.5-10.5 and in the presence of between 1.5 and 5% by weight of a manganese containing catalyst while passing substantially pure oxygen through the solution and while maintaining the temperature in the range of 25° C. to 78° C., and hydrolytically removing acyl and ester substituents from the ester of N-acylthyroxine obtained from the incubation step.

PCT publication No. WO 1996011904 discloses further improvements to a six stage process for production of sodium 1-thyroxine from 1-tyrosine as described in U.S. Pat. No. 2,889,363 and U.S. Pat. No. 2,889,364. These improvements comprise the oxidative coupling of a diiodo-1-tyrosine to form a biphenyl ether derivative, catalysed by a manganese salt in which the amine and acid functionality of the diiodo-1-tyrosine have been protected by suitable protecting groups, characterised in that the reaction is performed at a pressure of about 20 atmospheres in the presence of an organic amine additive using a gaseous oxidant comprising oxygen and optionally an inert diluent. The process optionally further comprises acid hydrolysis of the biphenyl ether derivative with hydrochloric acid to form 1-thyroxine hydrochloride salt and generation of sodium-1-thyroxine from the 1-thyroxine hydrochloride salt.

PCT publication number WO2009136249 provides a process for the preparation of levothyroxine sodium and comprises the steps of: iodinating 3, 5-diiodothyronine to obtain crude levothyroxine, followed by its conversion to disodium salt and acidifying the disodium salt to give pure levothyroxine. The purified levothyroxine is converted to levothyroxine sodium having reduced level of impurities. Levothyroxine sodium obtained by this invention is substantially free from d-enantiomer of thyroxine/3, 5-Diiodothyronine impurity. The process also reports the d-enantiomer of thyroxine/3, 5-Diiodothyronine levels below the limit of detection and liothyronine impurity below 0.5% wt/wt. The end product derived from this process is also free from coloured impurities.

Many patent and non-patent literature describe the use of an intermediate called Bis (p-anisyl)iodonium bromide in the preparation of Levothyroxine sodium. Hillmann (Z. Naturforch 1956; 11b:424-425) describes a process for the assembly of the biphenyl-ether system present in Levothyroxine, wherein a key coupling reaction is initiated between N-Acetyl 3,5-diiodo-L-tyrosine ethyl ester, derived from the stepwise protective conversion of amine as amide and acid as ester of 3,5 diido-L-tyrosine, and Bis (p-anisyl)iodonium bromide in the presence of copper metal or powder as a catalyst to afford (S)—N-acetyl-3,5-diiodo-4-p-methoxyphenoxyphenylalanine ethyl ester, with 87% yield. All the three protective groups in (S)—N-acetyl-3,5-diiodo-4-p-methoxyphenoxyphenylalanine ethyl ester, viz. acetamide, methyl ether, ethyl ester were cleaved using a mixture of Hydroiodic acid and Hydrobromic acid to give 3,5-Diiodothyronine. 3,5-Diiodothyronine on subsequent iodination with iodine gave L-thyroxine of an yield that corresponds to 92%.

The use of Bis (p-anisyl)iodonium bromide in the synthesis of thyroxine leads to the formation of an impurities called monobromo triiodo tyrosine and dibromo triiodo tyrosine which may be categorized as "Genotoxic impurities" based on the structure alerts. The levothyroxine compositions thus prepared are not generally preferred due to their genotoxic impurity content associated with purified Levothyroxine.

The aforesaid prior art processes cannot be considered for industrial scale preparation in view of their shortcomings such as less yield of the product, high expenses involved, pressure reactions which are less feasible for commercialization of the product, more number of reaction steps, cycle time and concerns about the purity of the endproduct. Hence there is a long-felt need for the development of an improved process that circumvents the above disadvantages and provides an industrially feasible, cost effective process involving the use of commercially available, simple raw materials in the process. At the same time it is also required that the process or technology developed should be easily adaptable for multikilo manufacturing plants for scaling-up the most demanding API product, Levothyroxine sodium at a very cheap cost, compared to the current import costs of the material and contemporary technologies in vogue.

OBJECTS OF THE INVENTION

It is an object of the present invention to provide an improved and industrially realisable process for preparing Levothyroxine Sodium.

Another object of the present invention is to provide an improved process for preparing Levothyroxine Sodium, which is simple, convenient and economical with commercial feasibility.

Yet another object of the present invention is to provide an improved process for preparing Levothyroxine Sodium by involving two new process intermediates namely 3,5-Diiodo L-Tyrosine copper complex and novel Bis (p-anisyl)iodonium Iodide.

A further object of the present invention is to provide an improved process for preparing Levothyroxine Sodium by using unprotected L-Tyrosine in the reaction.

Yet another object of the invention is to provide a process for preparing pure Levothyroxine Sodium that is devoid of any genotoxic impurities generated in the process.

Another object of the invention is to provide a process for preparing pure Levothyroxine Sodium obtained with liothyronine impurities <0.04%.

These and other objects of the present invention will be realized by way of practice of the invention described hereinafter.

SUMMARY OF THE INVENTION

According to an aspect of the present invention there is provided a process for the preparation of Levothyroxine Sodium comprising the steps of:
a. Coupling reaction between 3, 5-diiodo L-Tyrosine copper complex and novel Bis (p-anisyl) iodonium iodide in the presence of Diisopropylamine or other organic bases in n-Butanol or other alcoholic solvents to obtain 2-Amino-3-(3,5-diiodo-4-(4-methoxy phenoxy)phenyl)propanoic acid;
b. Demethylation of 2-Amino-3-(3,5-diiodo-4-(4-methoxyphenoxy)phenyl)propanoic acid using a mixture of Acetic acid and Hydroiodic acid to obtain 3,5-diiodothyronine;
c. Iodinizing 3,5-diiodothyronine with methanolic or other alcoholic monomethylamine and Iodine to obtain Levothyroxine;
d. Converting Levothyroxine to Levothyroxine Sodium in the presence of sodium hydroxide and n-butanol or other alcoholic solvents.

DETAILED DESCRIPTION OF THE INVENTION

It has been surprisingly found that by using two simple intermediates namely 3,5-Diiodo L-Tyrosine copper complex and novel Bis (p-anisyl)iodonium Iodide the process can be made economically and industrially feasible. The use of 3,5-Diiodo L-Tyrosine copper complex reduces the number of steps and increases the yield of the product while the use of novel Bis (p-anisyl)iodonium Iodide reduces the probable genotoxic impurities formation. In this method highly pure levothyroxine (99.9%) Sodium is obtained and the Liothyronine impurities observed, corresponds to only 0.04%.

The process for the preparation of Levothyroxine Sodium comprises the steps of:
a. Reacting 3,5-Diiodotyrosine dihydrate with aqueous copper sulphate solution to give 3, 5-diiodo L-Tyrosine copper complex
b. Initiating coupling reaction between 3, 5-diiodo L-Tyrosine copper complex and Bis (p-anisyl)iodonium iodide to give 2-Amino-3-(3,5-diiodo-4-(4-methoxy phenoxy)phenyl)propanoic acid in the presence of Diisopropylamine in n-Butanol.
c. Demethylation of 2-Amino-3-(3,5-diiodo-4-(4-methoxyphenoxy)phenyl)propanoic acid using a mixture of Acetic acid and Hydroiodic acid to give 3,5-diiodothyronine, an intermediate of L-Thyroxine and
d. Iodinizing 3,5-diiodothyronine with methanolic monomethylamine and Iodine to obtain Levothyroxine
e. Converting Levothyroxine to its sodium salt by using sodium hydroxide solution and n-butanol followed by filtering and drying to give pure Levothyroxine Sodium.

It will be apparent to the skilled person that certain changes and modifications may be practiced within the scope of the invention. Following examples illustratively demonstrate the process of the present invention, without posing any limitation to it.

Example-1

Preparation of 3,5-Diiodo L-Tyrosine Copper Complex

RBF was charged with 1200 ml of water and 15.01 gms of sodium hydroxide at 20-25° C. and stirred to get a clear solution. 100 gms of 3,5-Diiodotyrosine dihydrate was added and to the above mixture and stirred for an hour to get a clear solution. Copper sulphate solution (35.94 gms dissolved in 225 ml of water at 40° C.) was then added into the reaction mixture over a period of 1 hr and maintained at 20-25° C. for 1 hr. The resultant reaction mixture is filtered and washed with 1500 ml of DM water and dried under vacuum at 55-60° C. to get 95 gms of 3,5-Diiodo L-Tyrosine copper complex. The purity of obtained complex is NLT 97% with yield of 93-98%.

Example-2

Preparation of 3,5-Diiodothyronine

RBF was charged with 100 gms of 3,5-Diiodo L-Tyrosine copper complex and 1200 ml of water to which 1460 ml of n-Butanol was slowly added over a period of 30-45 min at 20-25° C. RBF was then charged with 36.6 gms of diisopropylamine at 20° C. and 92 gms of Bis(p-anisyl)iodonium iodide was added into the reaction mixture at 20-25° C. The reaction mixture was heated to 90° C. and maintained for 2 hrs at 90° C., then cooled to 20° C., followed by addition of 278 ml of toluene. To the above mixture 226 ml of 10% aqueous citric acid solution was added at 20-30° C. and maintained for 2 hrs at 20° C. followed by filtration and washing with 41 ml of water followed by 181 ml of Methyl isobutyl ketone wash to get 230 gms of wet 2-Amino-3-(3, 5-diiodo-4-(4-methoxyphenoxy)phenyl) propanoic acid. The above wet cake was stirred with 400 ml of water and 40 gms of citric acid for an hour at 20-25° C., filtered and washed with dilute citric acid solutions to get 160 gms of wet and pure 2-Amino-3-(3,5-diiodo-4-(4-methoxyphenoxy)phenyl)propanoic acid. The above wet cake was charged with 400 ml of acetic acid and 300 ml of Hydroiodic acid and the mixture was heated to 100° C. and maintained for 5 hrs and then cooled to 25-30° C. The reaction mixture was quenched in 3000 ml of 5% potassium bisulfite solution and 5% potassium dihydrogen phosphate mixture solution. The pH of the reaction mixture was adjusted to 4 using 250 ml of 50% aqueous lithium hydroxide solution and maintained for 30 min at 25-30° C. The reaction mixture was then filtered and washed with 500 ml of water followed by 200 ml of 1-Propanol (2 times), dried under vacuum at 50-55° C. for 12-15 hrs to get 80 gms of 3,5-Diiodothyronine of purity NLT 98% and yield corresponding to 71.5-76%.

Example-3

Preparation of Levothyroxine

RBF was charged with 100 gms of 3,5-Diiodothyronine and 1000 ml of methanolic monomethylamine at 25-30° C. and stirred for 15-20 min to get clear solution. The reaction mixture was then cooled to −8 to 0° C., and added with Iodine solution at −8 to 0° C. over a period of 2 hrs and maintained for 30-45 min at −8 to 0° C. The temperature of the reaction mixture was slowly brought to 15-20° C. and charged with 100 gms of sodium bisulphite followed by 300 gms of Potassium dihydrogen phosphate. The temperature of the reaction mixture was adjusted to 25-30° C. and maintained for 30-45 min at 25-30° C. The resultant mixture was filtered and washed with 200 ml of water followed by 200 ml of acetonitrile, dried under vacuum for 12-15 hrs at 55-60° C. to get 130 gms of Levothyroxine with purity NLT 98.5% and yield of 84.5-91.2%.

Example-4

Preparation of Levothyroxine Sodium

RBF was charged with 1000 ml of n-Butanol and 100 gms of Levothyroxine, cooled the contents to 5° C. and charged with 10 ml of concentrated sulphuric acid to get clear solution. The reaction mixture was filtered through 0.45 micron membrane filter and the filtrate was purged with ammonia gas to attain pH 8. The mixture was then heated to 60-65° C. and maintained for 1 hr at 60-65° C., followed by cooling to 40-45° C. and filtration at 45° C. The filtrate was then washed with 200 ml of hot n-Butanol. The wet cake is then charged with 250 ml of 1.5% aqueous Sodium hydroxide solution at 25-30° C. (pH maintained at 10), Followed by Slow addition of 800 ml of 1-propanol over a period of 10-15 min at 25-30° C., heated to 60-65° C. and maintained for 1 hour. Further the reaction mixture is cooled to 25-30° C. and maintained for 1 hour, filtered and washed with 100 ml of 1-propanol followed by vacuum drying at 45-50° C. for 12-15 hrs to get 85 gms of pure Levothyroxine sodium of 78-83% yield.

Example-5

Chemical Analysis of Levothyroxine Sodium

Three consecutive bulk batches of Levothyroxine sodium were prepared through the process described in the present invention and their yields were determined (Table-1). The product was chemically characterized by purity analysis through USP method-I and Method-II (depicted in Tables 2 and 3), $^1$H NMR (depicted in Structure-1 and Table-4), $^{13}$C NMR (Structure-2 and Table-5), Mass (Table-6), SOR (as per USP method) (Table-7), PSD (to show the consistency) (Table-8), Elemental analysis (Table-9).

TABLE 1

| S.No | Batch number | Input | Out put | Yield(m/w) |
|---|---|---|---|---|
| 1 | LVT-A101-045 | 50 gms | 42 gms | 44.33% |
| 2 | LVT-A101-046 | 50 gms | 4 gms | 43.27% |
| 3 | LVT-A101-058 | 50 gms | 41.5 gms | 43.80% |

Foot notes for table:
Input: 3,5-Diiodotyrosine dihydrate
Out Put: Levothyroxine sodium pentahydrate

TABLE 2

Purity by USP Method-I:

| Batch number | Purity | Liothyronine | Largest unidentified impurities | Total impurities |
|---|---|---|---|---|
| LVT-A101-045 | 99.96% | ND | 0.04% at 1.22 RRT | 0.04% |
| LVT-A101-046 | 99.90% | 0.07% | 0.03% at 1.22 RRT | 0.10% |
| LVT-A101-058 | 99.90% | 0.04% | 0.03% at 1.38 RRT | 0.10% |

TABLE 3

Purity by USP Method-II:

| Batch number | Purity | Liothyronine | Largest unidentified impurities | Total impurities |
|---|---|---|---|---|
| LVT-A101-045 | 99.91% | ND | 0.03% at 0.25 RRT | 0.09% |
| LVT-A101-046 | 99.84% | 0.06% | 0.03% at 1.16 RRT | 0.16% |
| LVT-A101-058 | 99.76% | 0.04% | 0.04% at 1.70 RRT | 0.24% |

Structure 1

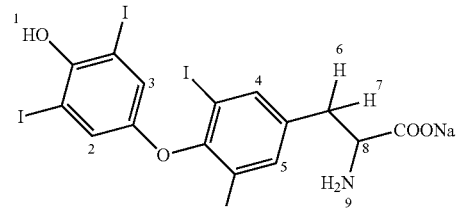

TABLE 4

Proton NMR:
$^1$H NMR SPECTRUM ASSIGNMENTS

| PROTON | CHEMICAL SHIFT (ppm) | MULTIPLICITY | # OF PROTONS |
|---|---|---|---|
| 4 & 5 | 7.79 | s | 2 |
| 2 & 3 | 6.93 | s | 2 |
| 8 | 3.42 | m | 1 |
| 6 | 3.10 – 3.07 | dd | 1 |
| 7 | 2.80 – 2.78 | dd | 1 |

The spectrum was obtained in DMSO-$d_6$ solvent at 400 MHz Bruker NMR spectrometer Structure 2

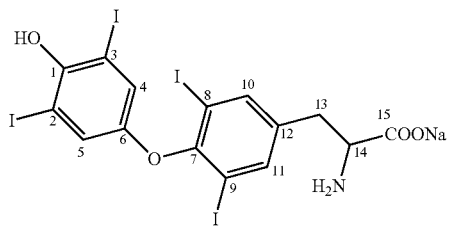

TABLE 5

$^{13}$C NMR $^{13}$C NMR SPECTRUM ASSIGNMENTS

| CARBON | DEPT | CHEMICAL SHIFT (ppm) |
|---|---|---|
| 15 | C | 172.34 |
| 7 | C | 159.87 |
| 6 | C | 152.31 |
| 1 | C | 143.69 |
| 10 & 11 | CH | 140.97 |
| 12 | C | 139.45 |
| 4 & 5 | CH | 124.72 |
| 8 & 9 | C | 92.18 |
| 2 & 3 | C | 88.49 |
| 14 | CH | 55.50 |
| 13 | CH$_2$ | 35.80 |

The spectrum was obtained in DMSO-d$_6$ solution at 100 MHz Bruker Avance NMR Spectrometer.

TABLE 6

Mass Analysis:

|  | M + 1 | M − 1 |
|---|---|---|
| LVT-A101-045 | 777.6 | 775.7 |
| LVT-A101-046 | 777.6 | 775.7 |
| LVT-A101-058 | 777.7 | 775.7 |

TABLE 7

Specific Optical rotation:

|  | As such | KF Results | On anhydrous basis |
|---|---|---|---|
| LVT-A101-045 | −5.2687 | 10.36 | −5.88 |
| LVT-A101-046 | −4.9364 | 10.0 | −5.48 |
| LVT-A101-058 | −5.2670 | 9.96 | −5.85 |

TABLE 8

PSD results:

|  | D(0.1) | D(0.5) | D(0.9) | D(1.0) |
|---|---|---|---|---|
| LVT-A101-045 | 1.044 μm | 2.317 μm | 4.711 μm | 8.401 μm |
| LVT-A101-046 | 1.000 μm | 2.060 μm | 4.047 μm | 7.301 μm |
| LVT-A101-058 | 0.868 μm | 1.816 μm | 3.654 μm | 6.33 μm |

TABLE 9

Elemental analysis: (on basis of pentahydrate)

|  | C (%) | H (%) | N (%) |
|---|---|---|---|
| Theoritical value | 20.27 | 2.27 | 1.58 |
| LVT-A101-045 (Observed value) | 20.27 | 2.28 | 1.63 |
| LVT-A101-046 (Observed value) | 20.66 | 2.31 | 1.61 |
| LVT-A101-058 (Observed value) | 20.37 | 2.26 | 1.54 |

The invention claimed is:

1. A process for the preparation of Levothyroxine Sodium comprising the steps of:
   a. Coupling reaction between 3, 5-diiodo L-Tyrosine copper complex and novel Bis (p-anisyl) iodonium iodide in the presence of Diisopropylamine or other organic bases in n-Butanol or other alcoholic solvents to obtain 2-Amino-3-(3,5-diiodo-4-(4-methoxy phenoxy)phenyl)propanoic acid;
   b. Demethylation of 2-Amino-3-(3,5-diiodo-4-(4-methoxyphenoxy)phenyl)propanoic acid using a mixture of Acetic acid and Hydroiodic acid to obtain 3,5-diiodothyronine;
   c. Iodinizing 3,5-diiodothyronine with methanolic or alcoholic monomethylamine and Iodine to obtain Levothyroxine;
   d. Converting Levothyroxine to Levothyroxine Sodium in the presence of sodium hydroxide and n-butanol or other alcoholic solvents.

2. The process as claimed in claim 1 wherein levothyroxine sodium is obtained with liothyronine levels below 0.04% wt/wt.

* * * * *